US 7,329,408 B2

(12) United States Patent
Houghton et al.

(10) Patent No.: US 7,329,408 B2
(45) Date of Patent: Feb. 12, 2008

(54) ELICITING HCV-SPECIFIC ANTIBODIES

(75) Inventors: Michael Houghton, Danville, CA (US); Mark Selby, San Francisco, CA (US); Sergio Abrignani, Vagliagli (IT); Jens Martin Heile, Ludwigsburg (DE); Derek O'Hagan, Berkeley, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 0 days.

(21) Appl. No.: 09/728,423

(22) Filed: Dec. 1, 2000

(65) Prior Publication Data

US 2002/0002272 A1     Jan. 3, 2002

Related U.S. Application Data

(60) Provisional application No. 60/185,055, filed on Feb. 25, 2000, provisional application No. 60/168,234, filed on Dec. 1, 1999.

(51) Int. Cl.
*A61K 39/29* (2006.01)

(52) U.S. Cl. .................. 424/228.1; 424/184.1; 424/204.1; 424/221.1; 435/5; 435/6; 435/7.1; 435/69.1; 435/320.1; 530/387.1

(58) Field of Classification Search ............ 424/184.1, 424/204.1, 228.1, 221.1; 435/5, 6, 7.1, 69.1, 435/320.1; 530/387.1
See application file for complete search history.

(56) References Cited

U.S. PATENT DOCUMENTS

| 5,350,671 | A |  | 9/1994 | Houghton et al. | |
| 6,121,020 | A | * | 9/2000 | Selby et al. | 424/189.1 |
| 6,306,405 | B1 | * | 10/2001 | O'Hagan et al. | 424/204.1 |
| 6,326,171 | B1 |  | 12/2001 | Selby et al. | |
| 6,521,423 | B1 |  | 2/2003 | Houghton et al. | |
| 6,562,346 | B1 |  | 5/2003 | Paliard et al. | |

FOREIGN PATENT DOCUMENTS

| EP | 0318216 | * | 5/1989 |
| WO | WO95/04301 |  | 2/1995 |
| WO | WO96/04301 A2 |  | 2/1996 |
| WO | WO96/05513 |  | 2/1996 |
| WO | WO98/50556 B2 |  | 11/1998 |
| WO | WO 01/30812 A3 |  | 5/2001 |

OTHER PUBLICATIONS

Wyatt J Virol Mar. 1998;72(3):1725-30.*
Inudof Vaccine 1996, vol. 14 1590- 1596.*
Ishi et al Hepatology 1998 vol. 28. pp. 1117-1120.*
Forns et al., Vaccine 1999 vol. 17, pp. 1992-2002.*
Nielson et al., AMPIS 1998 vol. 106, No. 6, pp. 636-646.*

Fournillier, A. et al., Expression of Noncovalent Hepatitis C Virus Envelope E1-E2 Complexes Is Not Required for the Induction of Antibodies with Neutralizing Properties following DNA J. Virol. 1999 73: 7497-7504.*

Masayuki et al., Transcripts from a single full-length cDNA clone of hepatitis C virus are infectious when directly transfected int the liver of a chimpanzee 1997 PNAS 94: 8738-8743.*

Singh, et al., A comparison of biodegradable microparticles and MF59 as systemic adjuvants for recombinant gD from HSV-2, Vaccine, vol. 16, Issue 19, Nov. 1998, pp. 1822-1827.*

Barnett, et al., Vaccination with HIV-1 gp120 DNA induces immune responses that are boosted by a recombinant gp120 protein subunit, Vaccine, vol. 15, Issue 8, Jun. 1997, pp. 869-873.*

Alter et al, "The Natural History of Community Acquired Hepatitis C in the United States," *N. Engl. J. Med.* 327:1899-1905 (1992).

Choo et al., "Genetic Organization and Diversity of the Hepatitis C Virus," *Proc. Natl. Acad. Sci. U.S.A.* 88:2451-2455 (1991).

Forns et al., "DNA Immunization of Mice and Macaques with Plasmids Encoding Hepatitis C Virus Envelope E2 Protein Expressed Intracellulary and on the Cell Surface," *Vaccine 17*:1992-2002 (1999).

Fourmiller et al., "Expression of Noncovalent Hepatitis C Virus Envelope E1-E2 Complexes is Not Required for the Induction of Antibodies with Neutralizing Properties Following DNA Immunization," *J. Virology* 73:7497-75504 (1999).

Inudoh et al., "Antigenicity of Hepatitis C Virus Envelope Proteins Expressed in Chines Hamster Ovary Cells," *Vaccine 14*:1590-1596 (1996).

Ishii et al., "High Titers of Antibodies Inhibiting the Binding of Envelope to Human Cells Correlate With Natural Resolution of Chronic Hepatitis C," *Hepatology 28*:1117-1120 (1998).

Ralston et al., "Characterization of Hepatitis C Virus Envelope Glycoprotein Complexes Expressed by recombinant Vaccinia Viruses," *J. Virology* 67:6753-6761 (1993).

Resnick and Koff, "Hepatitis C-Related Hepatocellular Carcinoma," *Arch. Interm. Med.* 153:1672-1677 (1993).

Rosa et al., "A Quantitative Test to Estimate Neutralizing Antibodies to the Hepatitis C Virus: Cytofluorimetric Assessment of Envelope Glycoprotein 2 Binding to Target Cells," *Proc. Natl. Acad. Sci. U.S.A.* 93:1759 (1996).

(Continued)

*Primary Examiner*—Bruce R. Campbell
*Assistant Examiner*—Myron G. Hill
(74) *Attorney, Agent, or Firm*—Robins & Pasternak LLP

(57) ABSTRACT

Described herein is a method of eliciting antibodies and neutralizing of binding antibodies against a hepatitis C virus (HCV) E1E2 or E2 antigen using HCV E2 or HCV E1E2 polypeptides and/or HCV E2 or E1E2 polynucleotides. Elicitation of anti-E2 antibodies and anti-E2 NOB antibodies can be used, inter alia, to provide model systems to optimize anti-E2 antibody responses and/or anti-E2 NOB antibody responses to HCV and to provide prophylactic or therapeutic treatment against HCV infection.

43 Claims, 4 Drawing Sheets

OTHER PUBLICATIONS

Seeff, "Natural History of Viral Hepatitis C," *Gastrointest. Dis.* 6:20-27 (1995).

Spaete et al., "Characterization of the Hepatitis C Virus E2/NS1 Gene Product Expressed in Mammalian Cells," *Virology 188*:819-830 (1992).

Heile, et al., "Evaluation of hepatitis C virus glycoprotein E2 for vaccine design: an endoplasmic reticulum-retained recombinant protein is superior to secreted recombinant protein and DNA-based vaccine candidates," J Virol. Aug. 2000; 74(15):6885-92.

Fournillier, et al., "Successful Induction of Antibodies With Neutralizing Properties Directed at Hepatitis C Virus Envelope Protein E2 Following DNA Immunization", Hepatology, vol. 30, No. 4, p. 451a, Oct. 1999 XP001030707, Abstract.

Geissler, et al., "Differential Cellular And Humoral Immune Responses to HCV Core And HBV Envelope Proteins After Genetic Immunizations Using Chimeric Constructs", Vaccine, 16(8):857-867 (1998).

Tedeschi, et al., "A Specific Antibody Response to HCV E2 Elicited in Mice By Intramuscular Inoculation of Plasmid DNA Containing Coding Sequences for E2", Hepatology, 25(2):459-462 (1997).

* cited by examiner

ELICITING HCV-SPECIFIC ANTIBODIES

CROSS-REFERENCE TO RELATED APPLICATION

This application is related to provisional patent applications Ser. No. 60/168,234, filed Dec. 1, 1999, and 60/185,055 filed Feb. 25, 2000 from which priority is claimed under 35 USC § 119(e)(1) and which are incorporated herein by reference in their entireties.

TECHNICAL AREA OF THE INVENTION

The invention relates to eliciting antibodies and neutralizing of binding antibodies against hepatitis C virus (HCV). More particularly, the invention relates to the use of HCV E1E2 and HCV E2 polypeptides or polynucleotides to elicit anti-E2 antibodies and anti-E2 neutralizing of binding antibodies in mammals.

BACKGROUND

Hepatitis C virus (HCV) is an important health problem with approximately 1% of the world's population infected with the virus. Over 75% of acutely infected individuals eventually progress to a chronic carrier state that can result in cirrhosis, liver failure, and hepatocellular carcinoma. A very small fraction of chronically infected patients naturally clear the HCV and resolve chronic hepatitis. See Alter et al. (1992) N. Engl. J. Med. 327:1899-1905; Resnick and Koff. (1993) Arch. Intern. Med. 153:1672-1677; Seeff (1995) Gastrointest. Dis. 6:20-27; Tong et al. (1995) N. Engl. J. Med. 332:1463-1466.

There is evidence of the existence of HCV-specific neutralizing antibodies during the course of infection with HCV. See Ishii et al. (1998) Hepatology. 28:1117-1120. Further, the appearance of and maintenance of high serum titers of anti-E2 neutralization of binding (NOB) antibodies in the course of chronic HCV infection has been correlated with protection from HCV infection, HCV clearance, and clinical resolution of HCV liver disease. Ishii et al. (1998); Rosa et al. (1996) Proc. Natl. Acad. Sci. USA 93:1759. However, to date, only purified HCV E2 polypeptides truncated at amino acid 715 have been shown to elicit anti-E2 NOB in animal studies. Foumillier et al. (1999) J. Virology 73:7497-75504. Thus, there remains a need for effective methods of eliciting anti-E2 NOB antibody titers.

SUMMARY

Described herein are methods of eliciting an immune response, particularly humoral immune responses (such as eliciting neutralization of binding (NOB) antibodies) against E2 and E1E2 antigens by administering polynucleotides encoding one or more of these antigens. Further, carbohydrate moieties are not necessary for E2 binding to human cells and only the monomeric nonaggregated fraction can bind to CD81. In preferred embodiments, protein and/or DNA immunization is accomplished using a mammalian cell-expressed, monomeric E2 protein purified from the intracellular fraction. Thus, it is an object of the invention to provide methods and reagents for eliciting anti-E2 antibodies and anti-E2 antibodies that neutralize binding of E2 to cells.

Thus, in one aspect, the invention includes a method of eliciting an immune response against a hepatitis C virus (HCV) E2 and/or E1E2 antigen (e.g., one or more purified polynucleotides encoding these antigens) comprising the step of (a) administering to a subject at least one polynucleotide encoding the E2 and/or E1E2 antigen(s). The polynucleotides encode HCV E2 and/or E1E2 polypeptides that are preferably non-secreted and, additionally, encode full-length E2. In preferred embodiments, the immune response is a humoral immune response, for example, a response that generates at least one neutralization of binding (NOB) antibody. In certain embodiments, more than one polynucleotide encoding different E2 or E1E2 antigens are administered. In various embodiments, the full-length (or non-truncated) E2 antigen(s) encoded by the polynucleotide(s) comprise/comprises amino acids 384-746 of an HCV polyprotein; amino acids 384-749 of an HCV polyprotein; 384-809 of an HCV polyprotein); or combinations thereof. In other embodiments, the antigen(s) encoded by the polynucleotide(s) include/includes E1 as well as E2 (e.g., constructs encoding amino acids 192-746 of an HCV polyprotein, amino acids 192-809 of an HCV polyprotein; amino acids 192-749 of an HCV polyprotein). Thus, the polynucleotides may encode one or more full-length E2 and one or more E1E2 antigens. In further embodiments, the antigen(s) is/are intracellularly produced (e.g., not secreted) truncated E2 (e.g., amino acids 384-715 of an HCV polyprotein; amino acids 384-661 of an HCV polyprotein, amino acids 340-674 of an HCV polyprotein). The polynucleotides may be, for example, DNA, plasmid DNA or other expression vector. In any of the methods described herein, the subject is or is not infected with one or more strains or HCV. Furthermore, in various embodiments, the methods may further comprise the step of administering an adjuvant (e.g., cardiotoxin) to the mammal.

In any of the methods described herein, the subject can be a mammal, for example a mouse, a rabbit, a guinea pig, a macaque, a baboon, a chimpanzee, and a human. The HCV encoding polynucleotides may be delivered by any suitable delivery mechanism (e.g., a biolistic delivery device, PLG microparticles, and the like). The polynucleotides may be delivered intramuscularly, subcutaneously, intraperitoneally, mucosally, intranasally, orally, and intradermally or the like.

In other embodiments, the methods further comprise the step of detecting the neutralizing of binding antibody. Further, in certain embodiments, the neutralizing of binding antibody inhibits binding of an E2 polypeptide to its cognate receptor by an amount which is greater relative to binding of the E2 polypeptide to its cognate receptor in the absence of the neutralizing of binding antibody, including but not limited to, a neutralizing of binding antibody that inhibits binding of the E2 polypeptide by at least 50% at a dilution of at least 1:70; a neutralizing of binding antibody that inhibits binding of the E2 polypeptide by at least 50% at a dilution of at least 1:140; a neutralizing of binding antibody that inhibits binding of the E2 polypeptide by at least 50% at a dilution of at least 1:300; a neutralizing of binding antibody that inhibits binding of the E2 polypeptide by at least 50% at a dilution of at least 1:600; a neutralizing of binding antibody that inhibits binding of the E2 polypeptide by at least 50% at a dilution of at least 1:800; and a neutralizing of binding antibody that inhibits binding of the E2 polypeptide by at least 50% at a dilution of at least 1:3,000.

The invention thus provides methods and reagents for eliciting anti-E2 antibodies and anti-E2 NOB antibodies. The methods and reagents are particularly advantageous for identifying epitopes of an HCV E2 or HCV E1E2 polypeptide associated with the generation of a strong anti-E2 antibody response and an anti-E2 NOB antibody response and for immunizing animals, including humans, against HCV.

These and other embodiments will be readily apparent to one skilled in the art in view of the teachings herein.

BRIEF DESCRIPTION OF THE DRAWINGS

FIGS. 3 and 4 show two separate experiments.

DETAILED DESCRIPTION OF THE INVENTION

Figure 1:
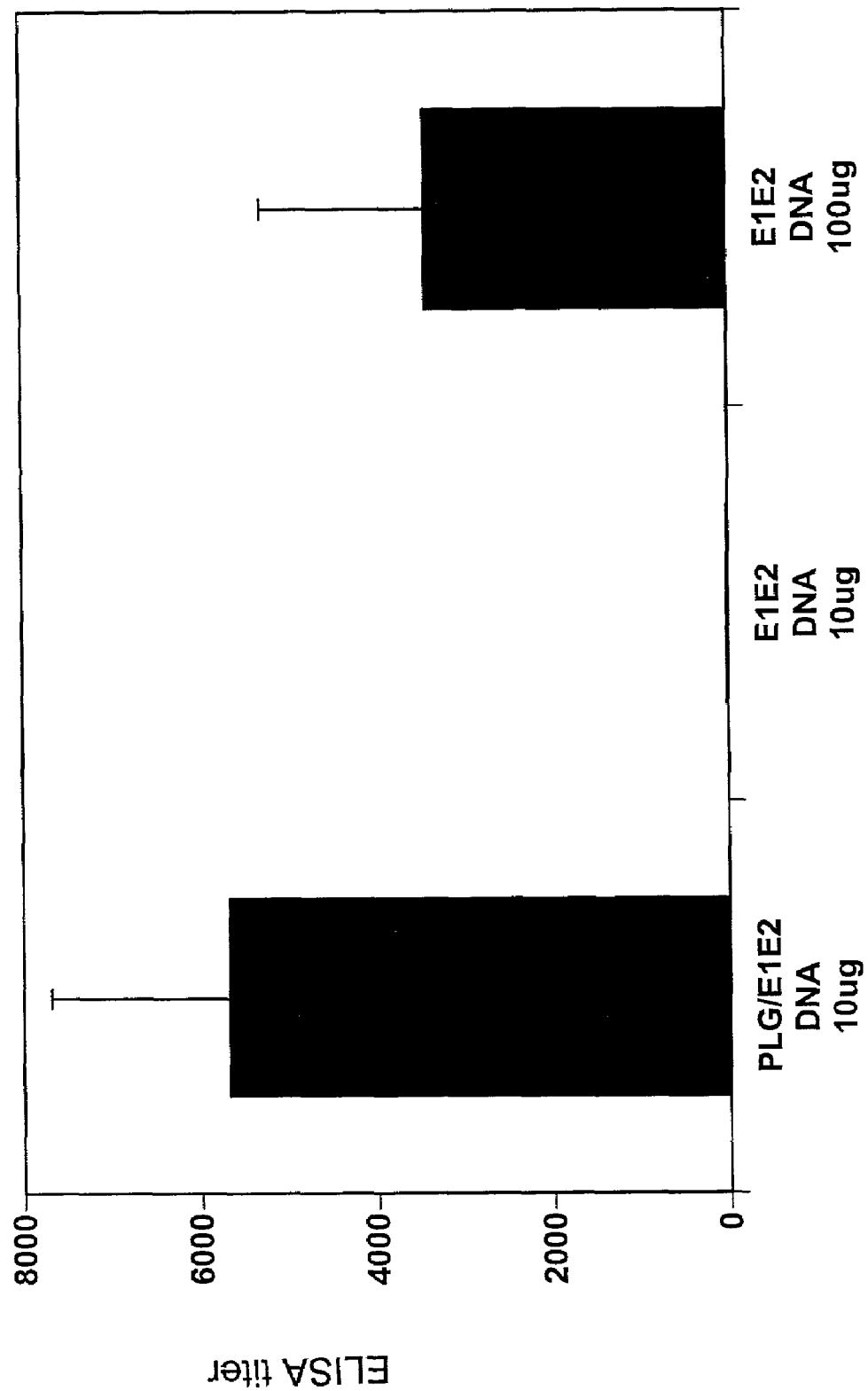
FIG. 1 is a graph depicting ELISA titers of mice immunized with 10 ug of E1E2/PLG DNA (left bar); 10 ug E1E2 DNA (middle bar) and 100 ug of E1E2/PLG DNA.

The practice of the present invention will employ, unless otherwise indicated, conventional methods of chemistry, biochemistry, recombinant DNA techniques and immunology, within the skill of the art. Such techniques are explained fully in the literature. See, e.g., Sambrook, et al., *Molecular Cloning: A Laboratory Manual* (2nd Edition); *Methods In Enzymology* (S. Colowick and N. Kaplan eds., Academic Press, Inc.); *DNA Cloning*, Vols. I and II (D. N. Glover ed.); *Oligonucleotide Synthesis* (M. J. Gait ed.); *Nucleic Acid Hybridization* (B. D. Hames & S. J. Higgins eds.); *Animal Cell Culture* (R. K. Freshney ed.); Perbal, B., *A Practical Guide to Molecular Cloning*.

All publications, patents and patent applications cited herein, whether above or below, are hereby incorporated by reference in their entireties.

It must be noted that, as used in this specification and the appended claims, the singular forms "a", "an" and "the" include plural referents unless the content clearly dictates otherwise. Thus, for example, reference to "an antigen" includes a mixture of two or more antigens, and the like.

I. Definitions

In describing the present invention, the following terms will be employed, and are intended to be defined as indicated below.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like. Furthermore, for purposes of the present invention, a "polypeptide" refers to a protein which includes modifications, such as deletions, additions and substitutions (generally conservative in nature), to the native sequence, so long as the protein maintains the desired activity. These modifications may be deliberate, as through site-directed mutagenesis, or may be accidental, such as through mutations of hosts which produce the proteins or errors due to PCR amplification.

An HCV polypeptide is a polypeptide, as defined above, derived from the HCV polyprotein. The polypeptide need not be physically derived from HCV, but may be synthetically or recombinantly produced. Moreover, the polypeptide may be derived from any of the various HCV strains, such as from strains 1, 2, 3 or 4 of HCV. A number of conserved and variable regions are known between these strains and, in general, the amino acid sequences of epitopes derived from these regions will have a high degree of sequence homology, e.g., amino acid sequence homology of at least about 30%-40%, preferably at least about 40%-60%, more preferably at least about 60%-70%, more preferably at least about 70%-75%, more preferably 80%-82%, more preferably 85%-90%, even more preferably 92%, still more preferably 95%, and most preferably 98% sequence identity to the reference sequence over a defined length of the molecules, as determined using the methods described herein when the two sequences are aligned.

Thus, for example, the term "E2" polypeptide refers to native E2 from any of the various HCV strains, as well as E2 analogs, muteins and immunogenic fragments, as described further below.

The terms "analog" and "mutein" refer to biologically active derivatives of the reference molecule, or fragments of such derivatives, that retain desired activity, such as the ability to stimulate a cell-mediated and/or humoral immune response, as defined below. In general, the term "analog" refers to compounds having a native polypeptide sequence and structure with one or more amino acid additions, substitutions (generally conservative in nature) and/or deletions, relative to the native molecule, so long as the modifications do not destroy immunogenic activity. The term "mutein" refers to peptides having one or more peptide mimics ("peptoids"), such as those described in International Publication No. WO 91/04282. Preferably, the analog or mutein has at least the same immunoactivity as the native molecule. Methods for making polypeptide analogs and muteins are known in the art and are described further below.

Particularly preferred analogs include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine.

Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5-10 conservative or non-conservative amino acid substitutions, or even up to about 15-25 conservative or non-conservative amino acid substitutions, or any integer between 5-25, so long as the desired function of the molecule remains intact. One of skill in the art may readily determine regions of the molecule of interest that can tolerate change by reference to Hopp/Woods and Kyte-Doolittle plots, well known in the art.

By "fragment" is intended a polypeptide consisting of only a part of the intact full-length polypeptide sequence and structure. The fragment can include a C-terminal deletion and/or an N-terminal deletion of the native polypeptide. An "immunogenic fragment" or "antigenic fragment" of a particular HCV protein will generally include at least about 5-10 contiguous amino acid residues of the full-length molecule, preferably at least about 15-25 contiguous amino acid residues of the full-length molecule, and most preferably at least about 20-50 or more contiguous amino acid residues of the full-length molecule, that define an epitope, or any integer between 5 amino acids and the full-length sequence, provided that the fragment in question retains immunogenic or antigenic activity, as measured by the assays described herein. For a description of various HCV epitopes, see, e.g., Chien et al., *Proc. Natl. Acad. Sci. USA* (1992) 89:10011-10015; Chien et al., *J. Gastroent. Hepatol* (1993) 8:S33-39; Chien et al., International Publication No. WO 93/00365; Chien, D. Y., International Publication No. WO 94/01778; commonly owned, allowed U.S. patent application Ser. Nos. 08/403,590 and 08/444,818.

The term "epitope" as used herein refers to a sequence of at least about 3 to 5, preferably about 5 to 10 or 15, and not more than about 1,000 amino acids (or any integer value between 3 and 1,000), which define a sequence that by itself or as part of a larger sequence, binds to an antibody generated in response to such sequence. There is no critical upper limit to the length of the fragment, which may comprise nearly the full-length of the protein sequence, or even a fusion protein comprising two or more epitopes from the HCV polyprotein. An epitope for use in the subject invention is not limited to a polypeptide having the exact sequence of the portion of the parent protein from which it is derived. Indeed, viral genomes are in a state of constant flux and contain several variable domains which exhibit relatively high degrees of variability between isolates. Thus the term "epitope" encompasses sequences identical to the native sequence, as well as modifications to the native sequence, such as deletions, additions and substitutions (generally conservative in nature).

Regions of a given polypeptide that include an epitope can be identified using any number of epitope mapping techniques, well known in the art. See, e.g., *Epitope Mapping Protocols* in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci.* USA 81:3998-4002; Geysen et al. (1986) *Molec. Immunol.* 23:709-715, all incorporated herein by reference in their entireties. Similarly, conformational epitopes are readily identified by determining spatial conformation of amino acids such as by, e.g., x-ray crystallography and 2-dimensional nuclear magnetic resonance. See, e.g., *Epitope Mapping Protocols, supra*. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., *Proc. Natl. Acad. Sci* USA (1981) 78:3824-3828 for determining antigenicity profiles, and the Kyte-Doolittle technique, Kyte et al., *J. Mol. Biol.* (1982) 157:105-132 for hydropathy plots.

As used herein, the term "conformational epitope" refers to a portion of a full-length protein, or an analog or mutein thereof, having structural features native to the amino acid sequence encoding the epitope within a full-length natural protein. Native structural features include, but are not limited to, glycosylation and three dimensional structure. Preferably, a conformational epitope is produced recombinantly and is expressed in a cell from which it is extractable under conditions which preserve its desired structural features, e.g. without denaturation of the epitope. Such cells include bacteria, yeast, insect, and mammalian cells. Expression and isolation of recombinant conformational epitopes from the HCV polyprotein are described in e.g., International Publication Nos. WO 96/04301, WO 94/01778, WO 95/33053, WO 92/08734, which applications are herein incorporated by reference in their entirety.

An "immunological response" to an HCV antigen (including both polypeptide and polynucleotides encoding polypeptides that are expressed in vivo) or composition is the development in a subject of a humoral and/or a cellular immune response to molecules present in the composition of interest. For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTLs"). CTLs have specificity for peptide antigens that are presented in association with proteins encoded by the major histocompatibility complex (MHC) and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

A composition or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host.

The term "antigen" refers to a composition which is capable of eliciting an immune response and may be, for example, a polypeptide or a polynucleotide encoding a polypeptide. The ability of a particular antigen to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art. See, e.g., Erickson et al., *J. Immunol.* (1993) 151:4189-4199; Doe et al., *Eur. J. Immunol.* (1994) 24:2369-2376; and the examples below. "Antigenic determinant" refers to the site on an antigen or hapten to which a specific antibody molecule or specific cell surface receptor binds.

Thus, an immunological response as used herein may be one which stimulates the production of CTLs, and/or the production or activation of helper T-cells. The antigen of interest may also elicit an antibody-mediated immune response, for example neutralization of binding (NOB) antibodies. Hence, an immunological response may include one or more of the following effects: the production of antibodies by B-cells; and/or the activation of suppressor T-cells and/or γδ T-cells directed specifically to an antigen or antigens present in the composition or vaccine of interest.

These responses may serve to neutralize infectivity, and/or mediate antibody-complement, or antibody dependent cell cytotoxicity (ADCC) to provide protection or alleviation of symptoms to an immunized host. Such responses can be determined using standard immunoassays and neutralization assays, well known in the art.

A "coding sequence" or a sequence which "encodes" a selected polypeptide, is a nucleic acid molecule which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A transcription termination sequence may be located 3' to the coding sequence.

A "nucleic acid" molecule or "polynucleotide" can include both double- and single-stranded sequences and refers to, but is not limited to, cDNA from viral, procaryotic or eucaryotic mRNA, genomic DNA sequences from viral (e.g. DNA viruses and retroviruses) or procaryotic DNA, and especially synthetic DNA sequences. The term also captures sequences that include any of the known base analogs of DNA and RNA.

"Operably linked" refers to an arrangement of elements wherein the components so described are configured so as to perform their desired function. Thus, a given promoter operably linked to a coding sequence is capable of effecting the expression of the coding sequence when the proper transcription factors, etc., are present. The promoter need not be contiguous with the coding sequence, so long as it functions to direct the expression thereof. Thus, for example, intervening untranslated yet transcribed sequences can be present between the promoter sequence and the coding sequence, as can transcribed introns, and the promoter sequence can still be considered "operably linked" to the coding sequence.

"Recombinant" as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

A "control element" refers to a polynucleotide sequence which aids in the expression of a coding sequence to which it is linked. The term includes promoters, transcription termination sequences, upstream regulatory domains, polyadenylation signals, untranslated regions, including 5'-UTRs and 3'-UTRs and when appropriate, leader sequences and enhancers, which collectively provide for the transcription and translation of a coding sequence in a host cell.

A "promoter" as used herein is a DNA regulatory region capable of binding RNA polymerase in a host cell and initiating transcription of a downstream (3' direction) coding sequence operably linked thereto. For purposes of the present invention, a promoter sequence includes the minimum number of bases or elements necessary to initiate transcription of a gene of interest at levels detectable above background. Within the promoter sequence is a transcription initiation site, as well as protein binding domains (consensus sequences) responsible for the binding of RNA polymerase. Eucaryotic promoters will often, but not always, contain "TATA" boxes and "CAT" boxes.

A control sequence "directs the transcription" of a coding sequence in a cell when RNA polymerase will bind the promoter sequence and transcribe the coding sequence into mRNA, which is then translated into the polypeptide encoded by the coding sequence.

"Expression cassette" or "expression construct" refers to an assembly which is capable of directing the expression of the sequence(s) or gene(s) of interest. The expression cassette includes control elements, as described above, such as a promoter which is operably linked to (so as to direct transcription of) the sequence(s) or gene(s) of interest, and often includes a polyadenylation sequence as well. Within certain embodiments of the invention, the expression cassette described herein may be contained within a plasmid construct. In addition to the components of the expression cassette, the plasmid construct may also include, one or more selectable markers, a signal which allows the plasmid construct to exist as single-stranded DNA (e.g., a M13 origin of replication), at least one multiple cloning site, and a "mammalian" origin of replication (e.g., a SV40 or adenovirus origin of replication).

"Transformation," as used herein, refers to the insertion of an exogenous polynucleotide into a host cell, irrespective of the method used for insertion: for example, transformation by direct uptake, transfection, infection, and the like. For particular methods of transfection, see further below. The exogenous polynucleotide may be maintained as a nonintegrated vector, for example, an episome, or alternatively, may be integrated into the host genome.

A "host cell" is a cell which has been transformed, or is capable of transformation, by an exogenous DNA sequence.

By "isolated" is meant, when referring to a polypeptide, that the indicated molecule is separate and discrete from the whole organism with which the molecule is found in nature or is present in the substantial absence of other biological macromolecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

The term "purified" as used herein preferably means at least 75% by weight, more preferably at least 85% by weight, more preferably still at least 95% by weight, and most preferably at least 98% by weight, of biological macromolecules of the same type are present.

"Homology" refers to the percent identity between two polynucleotide or two polypeptide moieties. Two DNA, or two polypeptide sequences are "substantially homologous" to each other when the sequences exhibit at least about 50%, preferably at least about 75%, more preferably at least about 80%-85%, preferably at least about 90%, and most preferably at least about 95%-98%, or more, sequence identity over a defined length of the molecules. As used herein, substantially homologous also refers to sequences showing complete identity to the specified DNA or polypeptide sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100.

Readily available computer programs can be used to aid in the analysis, such as ALIGN, Dayhoff, M. O. in *Atlas of Protein Sequence and Structure* M. O. Dayhoff ed., 5 Suppl. 3:353-358, National biomedical Research Foundation, Washington, D.C., which adapts the local homology algorithm of Smith and Waterman *Advances in Appl. Math.* 2:482-489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+ PDB+GenBank CDS translations+Swiss protein+Spupdate+ PIR. Details of these programs can be found at the following internet address: http://www.ncbi.nlm.gov/cgi-bin/BLAST.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

By "nucleic acid immunization" is meant the introduction of a nucleic acid molecule encoding one or more selected antigens into a host cell, for the in vivo expression of the antigen or antigens. The nucleic acid molecule can be introduced directly into the recipient subject, such as by injection, inhalation, oral, intranasal and mucosal administration, or the like, or can be introduced ex vivo, into cells which have been removed from the host. In the latter case, the transformed cells are reintroduced into the subject where an immune response can be mounted against the antigen encoded by the nucleic acid molecule.

As used herein, "treatment" refers to any of (i) the prevention of infection or reinfection, as in a traditional vaccine, (ii) the reduction or elimination of symptoms, and (iii) the substantial or complete elimination of the pathogen in question. Treatment may be effected prophylactically (prior to infection) or therapeutically (following infection).

The term "microparticle" as used herein, refers to a particle of about 100 nm to about 150 µm in diameter, more preferably about 200 nm to about 30 µm in diameter, and most preferably about 500 nm to about 10 µm in diameter. Preferably, the microparticle will be of a diameter that permits parenteral administration without occluding needles and capillaries. Microparticle size is readily determined by techniques well known in the art, such as photon correlation spectroscopy, laser diffractometry and/or scanning electron microscopy.

By "vertebrate subject" is meant any member of the subphylum cordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered. The invention described herein is intended for use in any of the above vertebrate species, since the immune systems of all of these vertebrates operate similarly.

Overview

It is a discovery of the present invention that HCV anti-envelope-2 glycoprotein (E2) antibody titers and neutralization of binding (NOB) antibody titers can be elicited by HCV E2 polypeptides (including full-length and truncated forms of E2 polypeptides), and HCV E1E2 polypeptides, as well as by polynucleotides encoding E2 and E1E2 polypeptides. Further, HCV E1E2 or HCV E2 polypeptides, with appropriate adjuvants, and polynucleotides elicit cellular immune responses, such as helper T-cell (CD4') responses and cytotoxic T-cell lymphocyte (CD8') responses.

Elicitation of HCV-specific antibodies by E1E2 and E2 polynucleotides and polypeptides provides both in vitro and in vivo model systems for the development of HCV vaccines, particularly for identifying HCV E2 and HCV E1E2 polypeptide epitopes associated with elicitation of a strong anti-E2 antibody titer and a strong anti-E2 NOB antibody titer. E1E2 and E2 polynucleotides or polypeptides also can be used to generate an immune response against an HCV in a mammal, particularly an anti-E2 antibody response and an anti-E2 NOB antibody response, for either therapeutic or prophylactic purposes.

E1E2 and E2 Polypeptides

The genome of a hepatitis C virus typically contains a single open reading frame of approximately 9,600 nucleotides, which is transcribed into a polyprotein. An HCV polyprotein is cleaved to produce at least ten distinct products, in the order of $NH_2$-Core-E1-E2-p7-NS2-NS3-NS4a-NS4b-NS5a-NS5b-COOH. The HCV E1 polypeptide is a glycoprotein and extends from approximately amino acid 192 to amino acid 383 (numbered relative to HCV-1). See Choo et al. (1991) *Proc. Natl. Acad. Sci.* USA 88:2451-2455. An HCV E2 polypeptide is a glycoprotein and extends from approximately amino acid 384 to amino acid 746 (numbered relative to HCV-1). See Choo et al. Thus, the term "full-length E2" or "not truncated E2" as used herein refers to polypeptides (and polynucleotides encoding these polypeptides) that include, at least, amino acids 384 to amino acid 746 of an HCV polyprotein (numbered relative to HCV-1). As will be evident from this disclosure, full length E2 polypeptides may include additional amino acids upstream and/or downstream of amino acids 384 and 746, such as amino acids 747-749 or 747-809. Non-limiting examples full-length E2 polypeptides include amino acids 384-746; 384-749 and 384-809 (as well as constructs encoding these polypeptides).

Typically, an E2 polypeptide with deletions at the C-terminal domain is secreted from a cell, while a full-length E2 polypeptide is retained within a cell. Forns et al. (1999) Vaccine 17:1992-2002; Spaete et al., *Virology* (1992) 188: 819-830; Ralston et al., *J. Virol.* (1993) 67:6753-6761). Since the E1 and E2 proteins are normally membrane-bound in these expression systems, experimenters had previously thought it desirable to produce secreted forms to facilitate purification of the proteins for further use. For example, an HCV E2 molecule, truncated at amino acid 661 and which is secreted from mammalian cells, has been described. Spaete et al., *Virology* (1992) 188:819-830. The production of truncated, secreted HCV E1 and E2 molecules has also been disclosed in International Publication No. WO 96/04301, published Feb. 15, 1996 and U.S. Pat. No. 6,121, 020. Inudoh et al., *Vaccine* (1996) 14:1590-1596, describes the production of an HCV E2 molecule lacking the C-terminal hydrophobic domain. This protein was secreted into culture medium and found to be more antigenic than intracellularly produced counterparts.

Described herein is the use of E2 polypeptides (and polynucleotide encoding these polypeptides), particularly non-secreted E2 and E1E2 polypeptides, which are capable of eliciting neutralization of binding (NOB) antibodies. E2 polypeptides of the invention can either be full-length E2 polypeptides, fragments of E2 polypeptides, or truncated segments of E2 polypeptides. For example, fragments of E2 polypeptides can comprise 6, 10, 25, 50, 75, 100, 150, 200, 250, 300, or 350 amino acids of E2 polypeptides. Truncated E2 polypeptides can be truncated at, for example, amino acid 550, 575, 600, 625, 650, 661, 675, 700, 715, 725 or 735 or 746of the HCV polyprotein. For purposes of the present invention, truncated E2 and E1E2 polypeptides which are normally secreted from the host cell are preferably anchored in the endoplasmic reticulum of the host cell, for example using a KDEL sequence at the C-terminus. Optionally, an E2 polypeptide can comprise additional amino acids, such as amino acids 747 through 749 of the HCV polyprotein or amino acids 747 through 809 of the HCV polyprotein. Preferably, an E2 polypeptide comprises amino acids 384-661, 384-746, 384-749, 384-715 or 384-809 of an HCV polyprotein.

An E2 polypeptide of the invention can be combined or synthesized with a truncated E1 polypeptide, a fragment of an E1 polypeptide, or a full length E1 polypeptide to form an E1E2 polypeptide. For example, fragments of E1 polypeptides can comprise 6, 10, 25, 50, 75, 100, 125, 150, or 175 amino acids of an E1 polypeptide. Preferably, an E1E2 polypeptide comprises amino acids 192-746, 192-749, 340-674, or 192-809 of an HCV polyprotein (numbered relative to HCV-1). The E1 and E2 polypeptides may be from the same or different HCV strains. E2 and E1E2 polypeptides can be recombinantly produced from constructs such as those described in U.S. Pat. No. 6,121,020.

E1E2 and E2 polypeptides comprise at least one epitope that is recognized by an anti-E2 antibody or an anti-E2 NOB antibody. Epitopes within E2 can be identified by several methods. For example, an E2 polypeptide can be isolated by methods such as immunoaffinity purification using a monoclonal antibody for E2. The isolated polypeptide sequence can then be screened. A series of short peptides, which together span the entire polypeptide sequence, can be prepared by proteolytic cleavage. By starting with, for example, 100-mer polypeptide fragments, each fragment can be tested for the presence of epitopes recognized in an anti-E2 NOB antibody assay or an anti-E2 enzyme-linked immunosorbent assay (ELISA). Progressively smaller and overlapping fragments can then be tested from an identified 100-mer to map the epitope of interest. NOB antibody assays are described in Example 1 and Rosa et al. (1996). ELISA assays are described in Example 3.

Various strains and isolates of HCV occur, and E1E2 or E2 polypeptides of any of these strains and isolates can be used in the present invention. Nucleic acid and amino acid sequences of HCV E1 and E2 genes and polypeptides are known in the art. For example, isolate HCV J1.1 is described in Kubo et al (1989) Japan. Nucl. Acids Res. 17:10367-10372; Takeuchi et al.(1990) Gene 91:287-291; Takeuchi et al. (1990) J. Gen. Virol. 71:3027-3033; and Takeuchi et al. (1990) Nucl. Acids Res. 18:4626. The complete coding sequences of two independent isolates, HCV-J and BK, are described by Kato et al., (1990) Proc. Natl. Acad. Sci. USA 87:9524-9528 and Takamizawa et al., (1991) J. Virol. 65:1105-1113, respectively.

Publications that describe HCV-1 isolates include Choo et al. (1990) Brit. Med. Bull. 46:423-441; Choo et al. (1991) Proc. Natl. Acad. Sci. USA 88:2451-2455 and Han Et al. (1991) Proc. Natl. Acad. Sci. USA 88:1711-1715. HCV isolates HC-J1 and HC-J4 are described in Okamoto et al. (1991) Japan J. Exp. Med. 60:167-177. HCV isolates HCT 18~, HCT 23, Th, HCT 27, EC1 and EC10 are described in Weiner et al. (1991) Virol. 180:842-848. HCV isolates Pt-1, HCV-K1 and HCV-K2 are described in Enomoto et al. (1990) Biochem. Biophys. Res. Commun. 170:1021-1025. HCV isolates A, C, D & E are described in Tsukiyama-Kohara et al. (1991) Virus Genes 5:243-254.

Preferably, an E1E2 or E2 polypeptide is produced recombinantly, for example in vitro or in vivo. A polynucleotide encoding an E1E2 or E2 polypeptide can be introduced into an expression vector which can be expressed in a suitable expression system using techniques well known in the art (and described below). A variety of bacterial, yeast, plant, mammalian, and insect expression systems are available in the art and any such expression system can be used. Optionally, a polynucleotide encoding an E1E2 or E2 polypeptide can be translated in a cell-free translation system.

If desired, an E1E2 or E2 polypeptide can be produced as a fusion protein, which can also contain other amino acid sequences, such as amino acid linkers or signal sequences, as well as ligands useful in protein purification, such as glutathione-S-transferase, histidine tag, and staphylococcal protein A. More than one E1E2 or E2 polypeptide can be present in a fusion protein. If desired, various combinations of E1E2 and E2 polypeptides from different HCV strains or isolates can be included in a fusion protein.

E1E2 and E2 Polynucleotides

E1E2 and E2 polynucleotides contain less than an entire HCV genome and can be RNA or single- or double-stranded DNA. Preferably, the polynucleotides are purified free of other components, such as proteins and lipids. E1E2 and E2 polynucleotides encode the E1E2 and E2 polypeptides described above. Polynucleotides of the invention can also comprise other nucleotide sequences, such as sequences coding for linkers, signal sequences, heterologous signal sequences, TMR stop transfer sequences, transmembrane domains, or ligands useful in protein purification such as glutathione-S-transferase, histidine tag, and staphylococcal protein A.

E1E2 and E2 polynucleotides can be isolated from a genomic library derived from nucleic acid sequences present in, for example, the plasma, serum, or liver of an HCV infected individual. E1E2 and E2 polynucleotides can be synthesized in the laboratory, for example, using an automatic synthesizer. An amplification method such as PCR can be used to amplify polynucleotides from either HCV genomic RNA or cDNA encoding E1E2 or E2 polypeptides.

E1E2 and E2 polynucleotides can comprise coding sequences for naturally occurring E1E2 or E2 polypeptides or can encode altered E1E2 or E2 sequences which do not occur in nature. If desired, E1E2 and E2 polynucleotides can be cloned into an expression vector and transformed into, for example, bacterial, yeast, insect, or mammalian cells so that the polypeptides of the invention can be expressed in and isolated from cell culture. E1E2 and E2 polynucleotides can be contained within a plasmid, such as pBR322, pUC, or ColE1, or an adenovirus vector, such as an adenovirus Type 2 vector or Type 5 vector. Optionally, other vectors can be used, including but not limited to Sindbis virus, simian virus 40, alphavirus vectors, and cytomegalovirus and retroviral vectors, such as murine sarcoma virus, mouse mammary tumor virus, Moloney murine leukemia virus, and Rous sarcoma virus. Bacterial vectors, such as Salmonella ssp., *Yersinia enterocolitica*, Shigella spp., *Vibrio cholerae*, *Mycobacterium* strain BCG, and *Listeria monocytogenes* can be used. Minichromosomes such as MC and MC1, bacteriophages, virus particles, virus-like particles, cosmids (plasmids into which phage lambda cos sites have been inserted) and replicons (genetic elements that are capable of replication under their own control in a cell) can also be used.

Polynucleotides contain less than an entire HCV genome and can be RNA or single- or double-stranded DNA. Preferably, the polynucleotides are isolated free of other components, such as proteins and lipids. Polynucleotides of the invention can also comprise other nucleotide sequences, such as sequences coding for linkers, signal sequences, or ligands useful in protein purification such as glutathione-S-transferase and staphylococcal protein A.

The expression constructs of the present invention may be used for nucleic acid immunization, to activate HCV-specific T cells, using standard gene delivery protocols. Methods for gene delivery are known in the art. See, e.g., U.S. Pat. Nos. 5,399,346, 5,580,859, 5,589,466, incorporated by reference herein in their entireties. Genes can be delivered either directly to the vertebrate subject or, alternatively, delivered ex vivo, to cells derived from the subject and the cells reimplanted in the subject. For example, the constructs can be delivered as plasmid DNA, e.g., contained within a plasmid, such as pBR322, pUC, or ColE1.

Additionally, the expression constructs can be packaged in liposomes prior to delivery to the cells. Lipid encapsulation is generally accomplished using liposomes which are able to stably bind or entrap and retain nucleic acid. The ratio of condensed DNA to lipid preparation can vary but will generally be around 1:1 (mg DNA:micromoles lipid), or more of lipid. For a review of the use of liposomes as carriers for delivery of nucleic acids, see, Hug and Sleight, *Biochim. Biophys. Acta.* (1991) 1097:1-17; Straubinger et al., in *Methods of Enzymology* (1983), Vol. 101, pp. 512-527.

Liposomal preparations for use with the present invention include cationic (positively charged), anionic (negatively charged) and neutral preparations, with cationic liposomes particularly preferred. Cationic liposomes are readily available. For example, N[1-2,3-dioleyloxy)propyl]-N,N,N-triethylammonium (DOTMA) liposomes are available under the trademark Lipofectin, from GIBCO BRL, Grand Island, N.Y. (See, also, Felgner et al., *Proc. Natl. Acad. Sci. USA* (1987) 84:7413-7416). Other commercially available lipids include transfectace (DDAB/DOPE) and DOTAP/DOPE (Boerhinger). Other cationic liposomes can be prepared from readily available materials using techniques well known in the art. See, e.g., Szoka et al., *Proc. Natl. Acad. Sci. USA* (1978) 75:4194-4198; PCT Publication No. WO 90/11092 for a description of the synthesis of DOTAP (1,2-bis(oleoyloxy)-3-(trimethylammonio)propane) liposomes. The various liposome-nucleic acid complexes are prepared using methods known in the art. See, e.g., Straubinger et al., in METHODS OF IMMUNOLOGY (1983), Vol. 101, pp. 512-527; Szoka et al., *Proc. Natl. Acad. Sci. USA* (1978) 75:4194-4198; Papahadjopoulos et al., *Biochim. Biophys. Acta* (1975) 394:483; Wilson et al., *Cell* (1979) 17:77); Deamer and Bangham, *Biochim. Biophys. Acta* (1976) 443:629; Ostro et al., *Biochem. Biophys. Res. Commun.* (1977) 76:836; Fraley et al., *Proc. Natl. Acad. Sci. USA* (1979) 76:3348); Enoch and Strittmatter, *Proc. Natl. Acad. Sci. USA* (1979) 76:145); Fraley et al., *J. Biol. Chem.* (1980) 255:10431; Szoka and Papahadjopoulos, *Proc. Natl. Acad. Sci. USA* (1978) 75:145; and Schaefer-Ridder et al., *Science* (1982) 215:166.

The DNA can also be delivered in cochleate lipid compositions similar to those described by Papahadjopoulos et al., *Biochem. Biophys. Acta.* (1975) 394:483-491. See, also, U.S. Pat. Nos. 4,663,161 and 4,871,488.

A number of viral based systems have been developed for gene transfer into mammalian cells. For example, retroviruses provide a convenient platform for gene delivery systems, such as murine sarcoma virus, mouse mammary tumor virus, Moloney murine leukemia virus, and Rous sarcoma virus. A selected gene can be inserted into a vector and packaged in retroviral particles using techniques known in the art. The recombinant virus can then be isolated and delivered to cells of the subject either in vivo or ex vivo. A number of retroviral systems have been described (U.S. Pat. No. 5,219,740; Miller and Rosman, *BioTechniques* (1989) 7:980-990; Miller, A. D., *Human Gene Therapy* (1990) 1:5-14; Scarpa et al., *Virology* (1991) 180:849-852; Burns et al., *Proc. Natl. Acad. Sci. USA* (1993) 90:8033-8037; and Boris-Lawrie and Temin, *Cur. Opin. Genet. Develop.* (1993) 3:102-109. Briefly, retroviral gene delivery vehicles of the present invention may be readily constructed from a wide variety of retroviruses, including for example, B, C, and D type retroviruses as well as spumaviruses and lentiviruses such as FIV, HIV, HIV-1, HIV-2 and SIV (see RNA Tumor Viruses, Second Edition, Cold Spring Harbor Laboratory, 1985). Such retroviruses may be readily obtained from depositories or collections such as the American Type Culture Collection ("ATCC"; 10801 University Blvd., Manassas, Va. 20110-2209), or isolated from known sources using commonly available techniques.

A number of adenovirus vectors have also been described, such as adenovirus Type 2 and Type 5 vectors. Unlike retroviruses which integrate into the host genome, adenoviruses persist extrachromosomally thus minimizing the risks associated with insertional mutagenesis (Haj-Ahmad and Graham, *J. Virol.* (1986) 57:267-274; Bett et al., *J. Virol.* (1993) 67:5911-5921; Mittereder et al., *Human Gene Therapy* (1994) 5:717-729; Seth et al., *J. Virol.* (1994) 68:933-940; Barr et al., *Gene Therapy* (1994) 1:51-58;

Berkner, K. L. *BioTechniques* (1988) 6:616-629; and Rich et al., *Human Gene Therapy* (1993) 4:461-476).

Molecular conjugate vectors, such as the adenovirus chimeric vectors described in Michael et al., *J. Biol. Chem.* (1993) 268:6866-6869 and Wagner et al., *Proc. Natl. Acad. Sci. USA* (1992) 89:6099-6103, can also be used for gene delivery.

Members of the Alphavirus genus, such as but not limited to vectors derived from the Sindbis and Semliki Forest viruses, VEE, will also find use as viral vectors for delivering the gene of interest. For a description of Sindbis-virus derived vectors useful for the practice of the instant methods, see, Dubensky et al., *J. Virol.* (1996) 70:508-519; and International Publication Nos. WO 95/07995 and WO 96/17072.

Other vectors can be used, including but not limited to simian virus 40, cytomegalovirus. Bacterial vectors, such as Salmonella ssp. *Yersinia enterocolitica*, *Shigella* spp., *Vibrio cholerae*, *Mycobacterium* strain BCG, and *Listeria monocytogenes* can be used. Minichromosomes such as MC and MC1, bacteriophages, cosmids (plasmids into which phage lambda cos sites have been inserted) and replicons (genetic elements that are capable of replication under their own control in a cell) can also be used.

The polynucleotides (e.g., expression constructs) described herein may also be encapsulated, adsorbed to, or associated with, particulate carriers, e.g., microparticles. Such carriers present multiple copies of a selected molecule to the immune system and promote trapping and retention of molecules in local lymph nodes. The particles can be phagocytosed by macrophages and can enhance antigen presentation through cytokine release. Microparticles for use herein will typically be formed from materials that are sterilizable, non-toxic and biodegradable. Such materials include, without limitation, poly(α-hydroxy acid), polyhydroxybutyric acid, polycaprolactone, polyorthoester, polyanhydride. Preferably, microparticles for use with the present invention are derived from a poly(α-hydroxy acid), in particular, from a poly(lactide) ("PLA") or a copolymer of D,L-lactide and glycolide or glycolic acid, such as a poly (D,L-lactide-co-glycolide) ("PLG" or "PLGA"), or a copolymer of D,L-lactide and caprolactone. The microparticles may be derived from any of various polymeric starting materials which have a variety of molecular weights and, in the case of the copolymers such as PLG, a variety of lactide:glycolide ratios, the selection of which will be largely a matter of choice, depending in part on the co-administered antigen. Examples of particulate carriers include those derived from polymethyl methacrylate polymers, as well as microparticles derived from poly(lactides) and poly(lactide-co-glycolides), known as PLG. See, e.g., Jeffery et al., *Pharm. Res.* (1993) 10:362-368; and McGee et al., *J. Microencap.* (1996). Polymethyl methacrylate polymers are nondegradable while PLG particles biodegrade by random nonenzymatic hydrolysis of ester bonds to lactic and glycolic acids which are excreted along normal metabolic pathways.

Recent studies have shown that PLG microparticles with entrapped antigens are able to elicit cell-mediated immunity. For example, microencapsulated human immunodeficiency virus (HIV) gp120 has been shown to induce HIV-specific CD4+ and CD8+ T-cell responses in mice (Moore et al., *Vaccine* (1995) 13:1741-1749). Similarly, microparticle-encapsulated ovalbumin has been shown to be capable of priming cellular immune responses in vivo and can induce mucosal IgA responses when administered orally (O'Hagan et al., *Vaccine* (1993) 11:149-154). Additionally, both antibody and T-cell responses have been induced in mice vaccinated with a PLG-entrapped *Mycobacterium* tuberculosis antigen (Vordermeier et al., *Vaccine* (1995) 13:1576-1582). Antigen-specific CTL responses have also been induced in mice using a microencapsulated short synthetic peptide from the circumsporozoite protein of *Plasmodium berghei*. Thus, in certain embodiments, the E2 and E1E2 polypeptides and/or polynucleotides are delivered using PLG microparticles (see, also, Example 4).

A wide variety of other methods can be used to deliver the expression constructs to cells. Such methods include DEAE dextran-mediated transfection, calcium phosphate precipitation, polylysine- or polyornithine-mediated transfection, or precipitation using other insoluble inorganic salts, such as strontium phosphate, aluminum silicates including bentonite and kaolin, chromic oxide, magnesium silicate, talc, and the like. Other useful methods of transfection include electroporation, sonoporation, protoplast fusion, liposomes, peptoid delivery, or microinjection. See, e.g., Sambrook et al., supra, for a discussion of techniques for transforming cells of interest; and Felgner, P. L., *Advanced Drug Delivery Reviews* (1990) 5:163-187, for a review of delivery systems useful for gene transfer. One particularly effective method of delivering DNA using electroporation is described in International Publication No. WO/0045823.

Additionally, biolistic delivery systems employing particulate carriers such as gold and tungsten, are especially useful for delivering the expression constructs of the present invention. The particles are coated with the construct to be delivered and accelerated to high velocity, generally under a reduced atmosphere, using a gun powder discharge from a "gene gun." For a description of such techniques, and apparatuses useful therefore, see, e.g., U.S. Pat. Nos. 4,945,050; 5,036,006; 5,100,792; 5,179,022; 5,371,015; and 5,478,744.

Compositions Comprising E1E2 and E2 Polypeptides or Polynucleotides The invention also provides compositions comprising E1E2 or E2 polypeptides or polynucleotides. Compositions of the invention preferably comprise a pharmaceutically acceptable carrier. The carrier should not itself induce the production of antibodies harmful to the host. Pharmaceutically acceptable carriers are well known to those in the art. Such carriers include, but are not limited to, large, slowly metabolized, macromolecules, such as proteins, polysaccharides such as latex functionalized sepharose, agarose, cellulose, cellulose beads and the like, polylactic acids, polyglycolic acids, polymeric amino acids such as polyglutamic acid, polylysine, and the like, animo acid copolymers, peptoids, lipitoids, and inactive virus particles.

Pharmaceutically acceptable salts can also be used in compositions of the invention, for example, mineral salts such as hydrochlorides, hydrobromides, phosphates, or sulfates, as well as salts of organic acids such as acetates, proprionates, malonates, or benzoates. Especially useful protein substrates are serum albumins, keyhole limpet hemocyanin, immunoglobulin molecules, thyroglobulin, ovalbumin, tetanus toxoid, and other proteins well known to those of skill in the art. Compositions of the invention can also contain liquids or excipients, such as water, saline, glycerol, dextrose, ethanol, or the like, singly or in combination, as well as substances such as wetting agents, emulsifying agents, or pH buffering agents. Liposomes can also be used as a carrier for a composition of the invention, such liposomes are described above.

If desired, co-stimulatory molecules which improve immunogen presentation to lymphocytes, such as B7-1 or B7-2, or cytokines such as GM-CSF, IL-2, and IL-12, can be included in a composition of the invention. Optionally, adjuvants can also be included in a composition. Adjuvants which can be used include, but are not limited to: (1) aluminum salts (alum), such as aluminum hydroxide, aluminum phosphate, aluminum sulfate, etc; (2) oil-in-water emulsion formulations (with or without other specific immunostimulating agents such as muramyl peptides (see below) or bacterial cell wall components), such as for example (a) MF59 (PCT Publ. No. WO 90/14837), containing 5% Squalene, 0.5% Tween 80, and 0.5% Span 85 (optionally containing various amounts of MTP-PE), formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+ CWS (Detox™); (3) saponin adjuvants, such as Stimulon™ (Cambridge Bioscience, Worcester, Mass.) may be used or particles generated therefrom such as ISCOMs (immunostimulating complexes); (4) Complete Freund's Adjuvant (CFA) and Incomplete Freund's Adjuvant (IFA); (5) cytokines, such as interleukins (e.g., IL-1, IL-2, IL-4, IL-5, IL-6, IL-7, IL-12, etc.), interferons (e.g., gamma interferon), macrophage colony stimulating factor (M-CSF), tumor necrosis factor (TNF), etc; (6) detoxified mutants of a bacterial ADP-ribosylating toxin such as a cholera toxin (CT), a pertussis toxin (PT), or an E. coli heat-labile toxin (LT), particularly LT-K63, LT-R72, CT-S109, PT-K9/G129; see, e.g., WO 93/13302 and WO 92/19265; (7) other substances that act as immunostimulating agents to enhance the effectiveness of the composition; and (8) microparticles with adsorbed macromolecules, as described, for example, in WO 00/06123 and WO 00/50006. Alum and MF59 are preferred. Microparticles such as PLG are described in more detail above.

As mentioned above, muramyl peptides include, but are not limited to, N-acetyl-muramyl-L-threonyl-D-isoglutamine (thr-MDP), -acetyl-normuramyl-L-alanyl-D-isoglutamine (CGP 11637, referred to nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), etc.

Optionally, the efficiency of delivery of E1E2 or E2 polynucleotides may be improved by injection of cardiotoxin, purified from the venom of *Naja nigricollis*, about one week prior to an E1E2 or E2 polynucleotide injection. A muscle is injected with from about 0.1 to 20 µM of cardiotoxin dissolved in a pharmacologically acceptable vehicle, such as 0.9% NaCl.

Thus, such recombinant or synthetic HCV polypeptides E2 and E1/E2 and polynucleotides can be used in vaccines and as diagnostics. Further, as detailed below, antibodies raised against these polypeptides can also be used as diagnostics, or for passive immunotherapy. In addition, antibodies to these polypeptides are useful for isolating and identifying HCV particles.

Antibodies

E1E2 or E2 polypeptides or polynucleotides of the invention can be used to elicit anti-E2 antibodies and/or anti-E2 NOB antibodies. Elicitation of anti-E2 and/or anti-E2 NOB antibodies can be used, inter alia, to provide model systems to optimize anti-E2 and/or anti-E2 NOB antibody responses to HCV and to provide prophylactic or therapeutic treatment against HCV infection.

Polyclonal antibodies can be produced by administering the fusion protein to a mammal, such as a mouse, a rabbit, a goat, or a horse. Serum from the immunized animal is collected and the antibodies are purified from the plasma by, for example, precipitation with ammonium sulfate, followed by chromatography, preferably affinity chromatography. Techniques for producing and processing polyclonal antisera are known in the art.

Monoclonal antibodies directed against HCV-specific epitopes present in the fusion proteins can also be readily produced. Normal B cells from a mammal, such as a mouse, immunized with, e.g., E1E2 or E2 polypeptide can be fused with, for example, HAT-sensitive mouse myeloma cells to produce hybridomas. Hybridomas producing HCV-specific antibodies can be identified using RIA or ELISA and isolated by cloning in semi-solid agar or by limiting dilution. Clones producing HCV-specific antibodies are isolated by another round of screening.

Antibodies, either monoclonal and polyclonal, which are directed against HCV epitopes, are particularly useful for detecting the presence of HCV or HCV antigens in a sample, such as a serum sample from an HCV-infected human. An immunoassay for an HCV antigen may utilize one antibody or several antibodies. An immunoassay for an HCV antigen may use, for example, a monoclonal antibody directed towards an HCV epitope, a combination of monoclonal antibodies directed towards epitopes of one HCV polypeptide, monoclonal antibodies directed towards epitopes of different HCV polypeptides, polyclonal antibodies directed towards the same HCV antigen, polyclonal antibodies directed towards different HCV antigens, or a combination of monoclonal and polyclonal antibodies. Immunoassay protocols may be based, for example, upon competition, direct reaction, or sandwich type assays using, for example, labeled antibody. The labels may be, for example, fluorescent, chemiluminescent, or radioactive.

The polyclonal or monoclonal antibodies may further be used to isolate HCV particles or antigens by immunoaffinity columns. The antibodies can be affixed to a solid support by, for example, adsorption or by covalent linkage so that the antibodies retain their immunoselective activity. Optionally, spacer groups may be included so that the antigen binding site of the antibody remains accessible. The immobilized antibodies can then be used to bind HCV particles or antigens from a biological sample, such as blood or plasma. The bound HCV particles or antigens are recovered from the column matrix by, for example, a change in pH.

Anti-E2 NOB Antibodies

HCV E1E2 and E2 polypeptides bind specifically to the surface of cells expressing a cognate receptor, e.g. human CD81, Flint et al. (1999) J. Virol. 73:6235. This binding is potentially responsible for HCV binding and subsequent infection of host cells. Rosa et al. (1996). HCV anti-E2 NOB antibodies inhibit ("neutralize") the binding of an HCV E2 to its cognate receptor by at least 10, 20, 30, 40, 50, 60, 70, 80, 90, or 100%.

There are at least two epitopes of E2 which can elicit an anti-E2 NOB antibody response. Anti-E2 NOB antibodies from patients infected with HCV types 1b, 2a, and 2b can neutralize the binding of an E2 polypeptide from HCV type 1a to mammalian cells. Therefore, at least one epitope responsible for eliciting an anti-E2 NOB antibody response is likely conserved in HCV genomes. Further, a monoclonal antibody against the HCV E2 hypervariable region 1 (HVR1) (amino acids 384-414) can partially neutralize binding of E2 to mammalian cells, suggesting the presence of an epitope in HVR1. Therefore, at least two neutralizing of binding epitopes, one of them which is hypervariable, exist on the E2 polypeptide.

HCV anti-E2 NOB antibodies can be detected and/or quantified using an anti-E2 NOB antibody assay as described in WO96/05513; Ishii et al. (1998); and Rosa et al. (1996). The anti-E2 NOB antibody assay detects inhibition of binding of an E2 polypeptide to cells which comprise a receptor for an HCV E2 polypeptide or to soluble CD81. For an assay, an E2 polypeptide is mixed with serial dilutions of serum from, for example, a mammal that has been infected with an HCV and/or has been vaccinated or treated for an HCV infection. The mammal can be, for example, a mouse, a rabbit, a guinea pig, a macaque, a baboon, a chimpanzee, or a human. The serum and E2 polypeptide are incubated. Cells, such as human T-cell lymphoma line Molt-4, hepatocarcinoma cell lines, or B cells, are added to the mixture and incubated. Optionally, cells which have been transfected with human CD81 can be used. After washing, neutralization of binding of E2 to the cells is assessed. The presence or amount of E2 bound to the cells is determined by incubating the cells with serum from the same species of mammal that provided the neutralizing serum, but which has been immunized with the particular E2 polypeptide used in the assay. The cells are then labeled using a fluorescent labeling compound, such as fluorescein isothiocyanate, phycoerythrin, rhodamine, phycocyanin, allophycocyanin, o-phthaldehyde, or fluorescamine. In a preferred embodiment, fluorescein isothiocyanate-conjugated antiserum to IgG is used as a detectable label. Binding of an E2 polypeptide to the cells is preferably detected indirectly using methods such as flow cytometry. An anti-E2 NOB antibody titer is defined as the serum dilution that results in at least 10 to 90%, and preferably at least 50% neutralization of E2 binding to its cognate receptor.

Anti-E2 Antibodies

Anti-E2 antibodies are antibody molecules that specifically and stably bind to an HCV E2 polypeptide or fragment thereof. HCV anti-E2 antibodies can be detected and/or quantified using for example, direct binding assays such as radioimmunoassay (RIA) or ELISA assays. For example, in an ELISA assay an E2 polypeptide is attached to a solid support, such as the wells of a plastic multi-well plate. A population of antibodies are labeled, added to the solid support and allowed to bind to the unlabeled E2 antigen, under conditions where non-specific adsorption is blocked, and any unbound antibody and other proteins are washed away. Antibody binding is detected by a reaction that converts a colorless substrate into a colored reaction product.

There is a direct correlation between the generation of anti-E2 NOB antibody titers and protection from HCV infection. Rosa et al. (1991); Ishii et al. (1998). Ordinarily, infection by an HCV does not elicit sustained high level anti-E2 NOB antibody titers. However, the small percentage of chronically HCV infected individuals who spontaneously resolve HCV infection do have sustained, high level anti-E2 NOB antibody titers. Thus, the appearance and maintenance of high serum titers of anti-E2 NOB antibodies in the course of chronic HCV infection is correlated with clearance and clinical resolution of HCV infection. The generation of an anti-E2 antibody response has been found to be important in providing a vaccination against infection by an HCV. Choo et al. (1994) Proc. Natl. Acad. Sci. USA 911294-1298.

Additionally, the generation of an anti-E1 titer may be important in protection from and the clearance of HCV infection.

Detection and/or quantification of anti-E2 antibody titers or anti-E2 NOB antibody titers after delivery of an E1E2 or E2 polypeptide or polynucleotide can be used to identify E2 epitopes that are particularly effective at eliciting anti-E2 antibody titers and/or anti-E2 NOB antibody titers. E1E2 or E2 epitopes responsible for a strong anti-E2 antibody and/or anti-E2 NOB antibody response to HCV can be identified by eliciting anti-E2 antibodies and/or anti-E2 NOB antibodies directed against E1E2 or E2 polypeptides of different lengths, e.g. terminating at amino acid 661, 715, 746, 749, or 809 of the HCV polypeptide, or removing amino acids from the amino terminus of the HCV polypeptide. Anti-E2 and anti-E2 NOB antibodies elicited by a particular E2 polypeptide epitope can then be tested using an anti-E2 ELISA assay or an anti-E2 NOB antibody assay to determine which polypeptides contain epitopes that are most effective at generating a strong response. E1E2 or E2 polypeptides or fusion proteins which contain these epitopes or polynucleotides encoding the epitopes can then be constructed and used to elicit a strong anti-E2 antibody response and/or a strong anti-E2 NOB antibody response.

Delivery

An E1E2 or E2 polypeptide or an E1E2 or E2 polynucleotide can be administered to a mammal, such as a mouse, for example CB6/F1 or C57B1/6 mice, rabbit, guinea pig, macaque, baboon, chimpanzee, or human, to elicit anti-E2 or anti-E2 NOB antibodies in vivo. Injection of an E1E2 or E2 polynucleotide is preferred. In addition to the practical advantages of simplicity of construction and modification, injection of an E1E2 or E2 polynucleotide(s) results in the synthesis of an E1E2 or E2 polypeptide in the host. Thus, the E1E2 or E2 polypeptide is presented to the host immune system with native post-translational modifications, structure, and conformation. An E1E2 or E2 polynucleotide is preferably delivered as "naked DNA." Administration of a polynucleotide or a polypeptide can be by any means known in the art, including intramuscular, intradermal, intraperitoneal, or subcutaneous injection, including injection using a biological ballistic gun ("gene gun"). Administration may also be intranasal or oral. Further, administration can be accomplished by electroporation. See, Mishimura (2000) *Vaccine* 18:675. Preferably, an E1E2 or E2 polynucleotide or polypeptide is accompanied by a protein carrier for oral administration. A combination of administration methods may also be used to elicit an anti-E2 and/or anti-E2 NOB antibody response.

Administration of E1E2 or E2 polypeptides or E1E2 or E2 polynucleotides can elicit an anti-E2 antibody titer and/or an anti-E2 NOB antibody titer in the mammal that lasts for at least 1 week, 2 weeks, 1 month, 2 months, 3 months, 4 months, 6 months, 1 year, or longer. Optionally, an anti-E2 or anti-E2 NOB antibody titer can be maintained in a mammal by providing one or more booster injections of the E1E2 or E2 polypeptide or E1E2 or E2 polynucleotide at 1 month, 2 months, 3 months, 4 months, 5 months, 6 months, 1 year, or more after the primary injection.

Preferably, an E1E2 or E2 polypeptide or E1E2 or E2 polynucleotide elicits an anti-E2 NOB antibody titer of at least 1:25, 1:50, 1:65, 1:70, 1:73, 1:75, 1:100, 1:140, 1:200, 1:300, 1:375, 1:400, 1:420, 1:500, 1:600, 1:700, 1:800, 1:900, 1:1,000, 1:3,000, 1:4,000, or higher.

Preferably, an E1E2 or E2 polypeptide or E1E2 or E2 polynucleotide elicits an anti-E2 antibody titer of at least 100, 150, 175, 200, 300, 400, 500, 750, 1,000, 1,500, 2,000, 3,000, 5,000, 10,000, 20,000, 30,000, 40,000, 50,000 (geometric mean titer) or higher.

A composition of the invention comprising an E1E2 or E2 polypeptide, E1 E2 or E2 polynucleotide, or a combination thereof is administered in a manner compatible with the particular composition used and in an amount which is effective to elicit an anti-E2 NOB antibody titer as detected by an anti-E2 NOB assay or an anti-E2 antibody titer as detected by an ELISA, as described above. An E1E2 or E2 polynucleotide is preferably injected intramuscularly to a large mammal, such as a baboon, chimpanzee, or human, at a dose of 1 ng/kg, 10 ng/kg, 100 ng/kg, 1000 ng/kg, 0.001 mg/kg, 0.1 mg/kg, or 0.5 mg/kg. An E1E2 or E2 polypeptide is preferably injected intramuscularly to a large mammal, such as a human, at a dose of 0.01, 0.05, 0.5, 0.75, 1.0, 1.5, 2.0, 2.5, 5 or 10 mg/kg. E1E2 or E2 polypeptides and/or E1E2 or E2 polynucleotides can be administered either to a mammal that is not infected with an HCV or can be administered to an HCV-infected mammal. The particular dosages of E1E2 or E2 polynucleotides or E1E2 or E2 polypeptides in a composition will depend on many factors including, but not limited to the species, age, and general condition of the mammal to which the composition is administered, and the mode of administration of the composition. An effective amount of the composition of the invention can be readily determined using only routine experimentation. In vitro and in vivo models described above can be employed to identify appropriate doses. The amount of E1E2 or E2 polynucleotides or E1E2 or E2 polypeptides used in the example below provides general guidance which can be used to optimize the elicitation of anti-E2 and/or anti-E2 NOB antibodies. If desired, co-stimulatory molecules or adjuvants can also be provided before, after, or together with the E1E2 or E2 compositions.

Immune responses of the mammal generated by the delivery of a composition of the invention, including elicitation of anti-E2 and anti-E2 NOB antibodies, can be enhanced by varying the dosage, route of administration, or boosting regimens. Compositions of the invention may be given in a single dose schedule, or preferably in a multiple dose schedule in which a primary course of vaccination includes 1-10 separate doses, followed by other doses given at subsequent time intervals required to maintain and/or reenforce an immune response, for example, at 1-3 months for a second dose, and optionally at 3-6 months for a third dose, and if needed, a subsequent dose or doses after several months. Similarly, in some embodiments, an immune response is elicited using a prime-boost strategy (one or more DNA-prime and one or more protein-boosts).

The following are provided of exemplification purposes only and are not intended to limit the scope of the invention described in broad terms above. All documents cited in this disclosure are incorporated herein by reference.

EXAMPLES

Example 1

Immunization with a Truncated E2 Polypeptide or Polynucleotide Elicits an Anti E2-NOB Antibody Titer E2 Compositions Polynucleotides encoding full length HCV E2 or HCV E2 truncated at amino acid 661 or 715 were ligated into plasmid vector pnewCMV. pnewCMV is a pUC19-based cloning vector comprising the following elements: an SV40 origin of replication, a human CMV enhancer/promoter, a human CMV intron, a human tissue plasminogen activator (tPA) leader, and a bovine growth hormone poly A terminator. Isolated and purified pnewCMV vectors containing an E2 insert were dissolved in sterile 0.9% saline buffer.

An E2 polypeptide truncated at amino acid 715 was recombinantly produced and purified using an S-Sepharose column. The E2 polypeptide truncated at amino acid 661 is a recombinantly produced secreted polypeptide available from Abbott Laboratories.

Cardiotoxin, purified from venom of *Naja nigricollis*, was obtained from Latoxin (France). The cardiotoxin was diluted in 0.9% NaCl to a final concentration of 10 µM.

Immunization

CB6/F1 mice were split into 6 groups of 10 or 12 mice each. Group 1 mice received injections of 100 µg of plasmid DNA containing a polynucleotide encoding full length E2 (pnewCMVE2-746 DNA). Group 2 received injections of 100 µg of plasmid DNA containing a polynucleotide encoding E2 truncated at amino acid 715 (pnewCMVE2-715 DNA). Group 3 received injections of 100 µg of plasmid DNA containing a polynucleotide encoding E2 truncated at amino acid 661 (pnewCMVE2-661 DNA). Group 4 received injections of 1 µg of E2 polypeptide truncated at amino acid 715 (CHO E2-715 1 µg). Group 5 received injections of 1 µg of E2 polypeptide truncated at amino acid 661 (CHO E2-661). Group 6 received injections of 5 µg of E2 polypeptide truncated at amino acid 715 (CHO E2-715 5 µg). The E2 compositions were administered according the schedule in Table 1.

TABLE 1

|  | pnewCMV E2-746 | pnewCMV E2-715 | pnew CMVE2-661 | CHO E2-715 1 µg | CHO E2-661 | CHO-E2-715 5 µg |
|---|---|---|---|---|---|---|
| Day 1 | First cardiotoxin injection | First cardiotoxin injection | First cardiotoxin injection |  |  |  |
| Day 7 | First DNA injection | First DNA injection | First DNA injection | First polypeptide injection | First polypeptide injection | First polypeptide injection |
| Day 22 | Second cardiotoxin injection | Second cardiotoxin injection | Second cardiotoxin injection |  |  |  |

TABLE 1-continued

| | pnewCMV E2-746 | pnewCMV E2-715 | pnew CMVE2-661 | CHO E2-715 1 μg | CHO E2-661 | CHO-E2-715 5 μg |
|---|---|---|---|---|---|---|
| Day 29 | Second DNA injection | Second DNA injection | Second DNA injection | Second polypeptide injection | Second polypeptide injection | |
| Day 41 | | | | | | Second polypeptide injection |
| Day 69 | | | | | | Third polypeptide injection |
| Day 78 | Third cardiotoxin injection | Third cardiotoxin injection | Third cardiotoxin injection | | | |
| Day 85 | Third DNA injection | Third DNA injection | Third DNA injection | Third polypeptide injection | Third polypeptide injection | |

Cardiotoxin, 0.05 ml of 10 μM solution, was injected intramuscularly into each mouse tibialis anterior muscle. E2 plasmid in 0.9% saline (1 mg/ml) was injected intramuscularly into each mouse tibialis anterior muscle (0.05 ml into each muscle), for a total of approximately 100 μg of DNA injected. E2 polypeptide at approximately 0.02 mg/ml or 0.1 mg/ml was combined 1:1 with MF59-0 adjuvant and 0.05 ml was injected intramuscularly into each tibialis anterior muscle, for a total of approximately 1 μg or 5 μg of polypeptide injected. For mice in groups 1-5, 0.2 ml of blood was obtained from each mouse on day 21, day 43, and day 99. For mice in group 6, 0.2 ml of blood was obtained from each mouse on day 55 and day 83.

Detection and Measurement of Anti-E2 NOB Titers

Recombinant E2 polypeptide was produced and purified from Chinese hamster ovary (CHO) cells expressing HCV type 1a complementary DNA (cDNA) encoding the envelope region of E2 (amino acids 384-715). Molt-4 cells ($10^5$ per well) were pelleted in 96 well U-bottom microplates by centrifugation at 200×g for 5 minutes at 4° C. 20 μl of E2 polypeptide diluted in PBS at different concentrations was mixed with various dilutions of sera from mice that were either infected with HCV or were immunized with HCV recombinant proteins. After incubation at 4° C. for 1 hour the Molt-4 cells were added and incubated for 1 hour at 4° C. Non-bound HCV proteins and antibodies were removed by two centrifugations in PBS at 200×g for 5 minutes at 4° C. Cells were subsequently incubated for 30 minutes at 4° C. with 1/100 dilution of sera from mice that had been immunized with HCV envelope recombinant proteins. Where possible, the corresponding pre-immune sera were used as controls. The cells were washed twice in PBS and incubated for 30 minutes with appropriate dilutions for fluorescein isothiocyanate-conjugated antiserum to IgG. Cells were washed in PBS at 4° C. and resuspended in 100 μl PBS.

Cell-bound fluorescence was analyzed with a FACScan flow cytometer (Becton Dickinson) using the Lysis II software program from Becton Dickinson. The mean fluorescence intensity (MFI) of the cell population was calculated. The MFI directly relates to the surface density of fluorescently labeled HCV proteins bound to the cells. In this example, the NOB antibody titer is defined as the serum dilution that show 50% neutralization of E2 binding.

The average anti-E2 NOB antibody titer of mice exhibiting an NOB titer are reported in Table 2. The number of mice of each group exhibiting an anti-E2 NOB antibody titer are shown in brackets under the average anti-E2 NOB antibody titer.

TABLE 2

| | 50% Anti-E2 NOB antibody Titer | | |
|---|---|---|---|
| Composition Administered | NOB Titer After First E2 Composition Injection | NOB Titer After Second E2 Composition Injection | NOB Titer After Third E2 Composition Injection |
| pnewCMVE2-746 | 0 | 1:73 [7/10] | 1:140 [9/10] |
| pnewCMVE2-715 | 0 | 1:50 [9/10] | 1:75 [7/10] |
| pnewCMVE2-661 | 0 | 1:66 [10/10] | 1:70 [8/10] |
| CHO E2-715 1 μg | 0 | 1:375 [10/10] | 1:800 [10/10] |
| CHO E2-661 | 0 | 1:65 [4/10] | 1:420 [10/10] |
| CHO E2-715 5 μg | 0 | 1:3000 [11/12] | 1:4200 [11/12] |

Table 2 demonstrates that immunization with plasmid DNA encoding E2 and truncations thereof elicits an anti-E2 NOB antibody titer. An anti-E2 NOB antibody titer was elicited even though E2 was delivered by plasmid DNA. Anti-E2 NOB antibodies have not previously been shown to be elicited by plasmids comprising fall length E2 polypeptides. Table 2 further demonstrates that immunization with E2 polypeptides elicits an anti-E2 NOB antibody titer, even though the E2 polypeptides were truncated at amino acid 715 or 661.

Example 2

Immunization with DNA Encoding an E1E2 Polypeptide Elicits an Anti-E2-NOB Antibody Titer E1E2 Compositions Polynucleotides encoding E1E2 were ligated into plasmid vector pnewCMV. The polynucleotides encoded amino acids 192-746 (pnewCMVE1E2-746), amino acids 192-749 (pnewCMVE1E2-749), amino acids 192-809 (pnewCMVE1E2-809) of an HCV polyprotein (amino acids numbered relative to HCV-1). Isolated and purified pnewCMV vectors containing and E1E2 insert were dissolved in sterile 0.9% saline buffer.

Immunization

Groups of CB6/F1 mice were intramuscularly injected with cardiotoxin at 0, 4, and 8 weeks as described in Example 1. The mice were injected with 100 μg of plasmid DNA (pnewCMVE1E2-746, pnewCMVE1E2-749, or pnewCMVE1E2-809) at 1, 5, and 9 weeks as described in Example 1.

Detection and Measurement of Anti-E2 NOB Titers

The average anti-E2 NOB antibody titer for each group of mice was determined as described in Example 1. The results are shown in Table 3. The number of mice of each group exhibiting an anti-E2 NOB antibody titer are shown in brackets under the average anti-E2 NOB antibody titer.

TABLE 3

| Composition Administered | 50% Anti-E2 NOB Antibody Titer |
|---|---|
| | NOB Titer After Third E1E2 Composition Injection |
| pnewCMVE1E2-746 | 1:125 [2/12] |
| pnewCMVE1E2-749 | 1:95 [12/12] |
| pnewCMVE1E2-809 | 1:75 [9/12] |

Table 3 demonstrates that immunization with plasmid DNA encoding E1E2 elicits an anti-E2 NOB antibody titer. An anti-E2 NOB antibody titer was elicited even though E1E2 was delivered by plasmid DNA. Anti-E2 NOB antibodies have not previously been shown to be elicited by plasmids comprising full length E1E2 polypeptides.

Example 3

Immunization with DNA Encoding an E1E2 Polypeptide or DNA Encoding an E2 Polypeptide Elicits an Anti-E2 Antibody Titer E1E2 and E2 Compositions The DNA plasmids pnewCMVE2-746, pnewCMVE1E2-746, pnewCMVE1E2-749, and pnewCMVE1E2-749, and pnewCMVE1E2-809 were prepared as described in Examples 1 and 2.

Immunization

Groups of CB6/F1 mice were intramuscularly injected with cardiotoxin at 0, 4, and 8 weeks as described in Example 1. The mice were injected with 100 μg of plasmid DNA (pnewCMVE2-746, pnewCMVE1E2-746, pnewCMVE1E2-749, or pnewCMVE1E2-809) at 1, 5, and 9 weeks as described in Example 1.

Detection and Measurement of Anti-E2 Antibody Titers

The detection and measurement of anti-E2 antibodies was accomplished by ELISA, essentially as described in Ishii et al. (1998) Hepatology 28:1117-20, and Tedeschi et al. (1997) Hepatology 25:459-462. Briefly, recombinant CHO cell produced HCV E2, or E1/E2 antigens were diluted in PBS and coated on the wells of microtiter plates. Test mouse sera were diluted in sample diluent and incubated on the plates at for one hour at 37° C. The wells were washed with plate wash buffer. Monoclonal murine anti-human IgG antibody conjugated to horseradish peroxidase was added to each well. O-Phenylenediamine dihydrochloride (OPD) and hydrogen peroxide were added to the wells. The results were read using a microtitre plate reader at $^{492}/_{620}$ nm (Tetertek MCC/340; Flow Laboratories). The cutoff optical density (OD) values for these antigens were determined to be the mean of negative samples (prebleeds) plus seven times the standard deviation of the mean OD. The titers of the tested samples were determined as the relatively linear range signal OD/cutoff OD times the dilution factors. The geometric mean titer (GMT) is reported in Table 4.

TABLE 4

| Immunogen Administered | ELISA Anti-E2 Titer After Third Immunogen Injection (Geometric Mean Titer) |
|---|---|
| pnewCMVE1E2-746 | 1548 |
| pnewCMVE1E2-749 | 1217 |
| pnewCMVE1E2-809 | 173 |
| pnewCMVE2-746 | 1062 |

Table 4 demonstrates that immunization with plasmid DNA encoding E1E2 or E2 elicits an anti-E2 antibody titer. An anti-E2 antibody titer was elicited even though full length E1E2 or E2 was delivered by plasmid DNA. Anti-E2 antibodies have not previously been shown to be elicited by plasmids comprising full-length E1E2 or E2 polypeptides, where the polypeptide does not comprise a p7 polypeptide.

Example 4

Immunization with PLG-Delivered DNA

The polylactide-co-glycolide (PLG) polymers were obtained from Boehringer Ingelheim, U.S.A. The PLG polymer used in this study was RG505, which has a copolymer ratio of 50/50 and a molecular weight of 65 kDa (manufacturers data). Cationic microparticles with adsorbed DNA were prepared using a modified solvent evaporation process, essentially as described in Singh et al., Proc. Natl. Acad. Sci. USA (2000) 97:811-816. Briefly, the microparticles were prepared by emulsifying 10 ml of a 5% w/v polymer solution in methylene chloride with 1 ml of PBS at high speed using an IKA homogenizer. The primary emulsion was then added to 50 ml of distilled water containing cetyl trimethyl ammonium bromide (CTAB) (0.5% w/v). This resulted in the formation of a w/o/w emulsion which was stirred at 6000 rpm for 12 hours at room temperature, allowing the methylene chloride to evaporate. The resulting microparticles were washed twice in distilled water by centrifugation at 10,000 g and freeze dried. Following preparation, washing and collection, DNA was adsorbed onto the microparticles by incubating 100 mg of cationic microparticles in a 1 mg/ml solution of DNA at 4° C. for 6 hours. The microparticles were then separated by centrifugation, the pellet washed with TE buffer and the microparticles were freeze dried, resuspended and administered to animal subjects.

Figure 2:
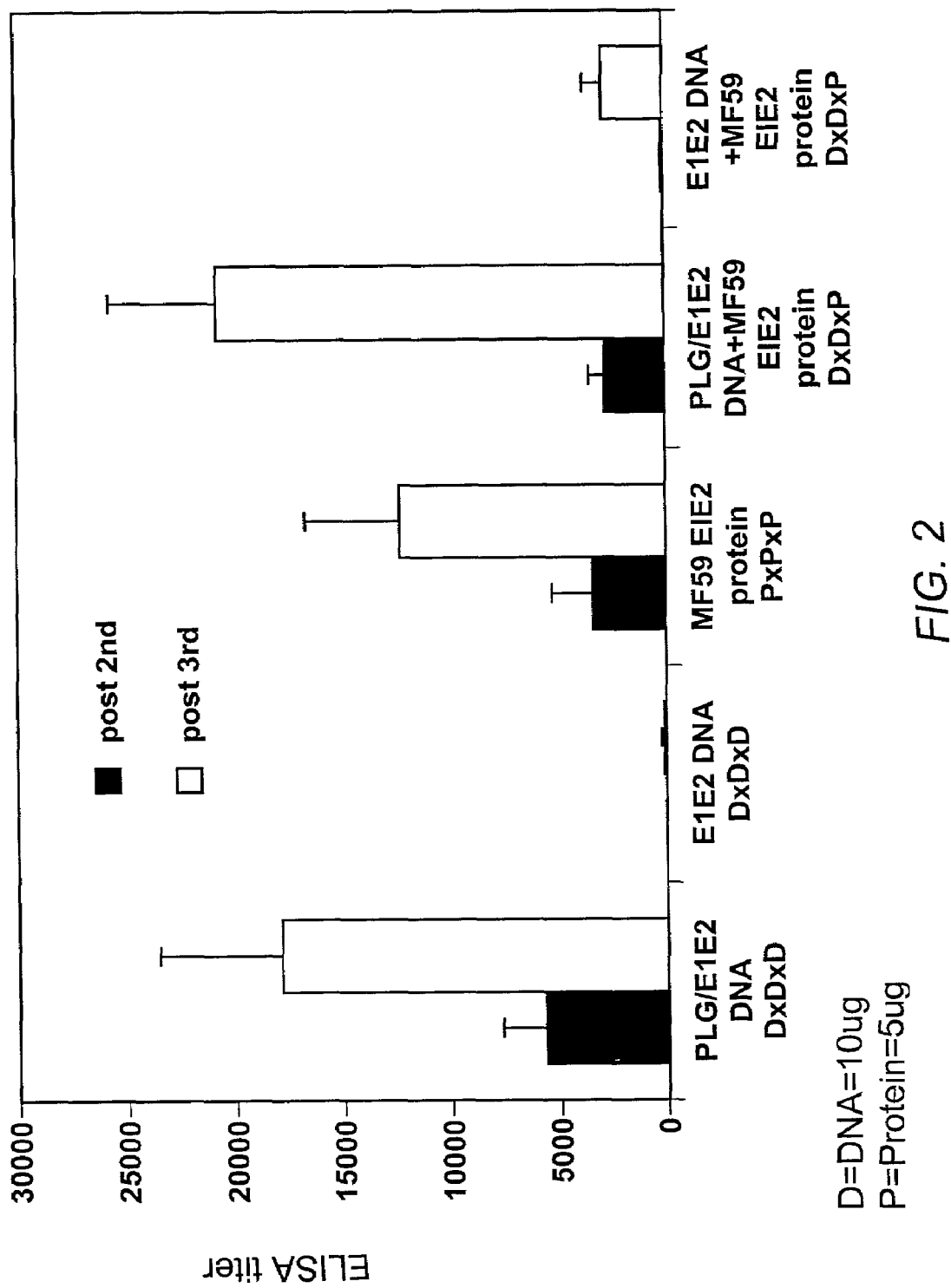
FIG. 2 is a graph depicting ELISA titers of mice immunized with E1E2 DNA and/or protein in various adjuvants. The black bars depict titers post-2nd boost and the white bars depict titers post-3rd boost.
Figure 3:
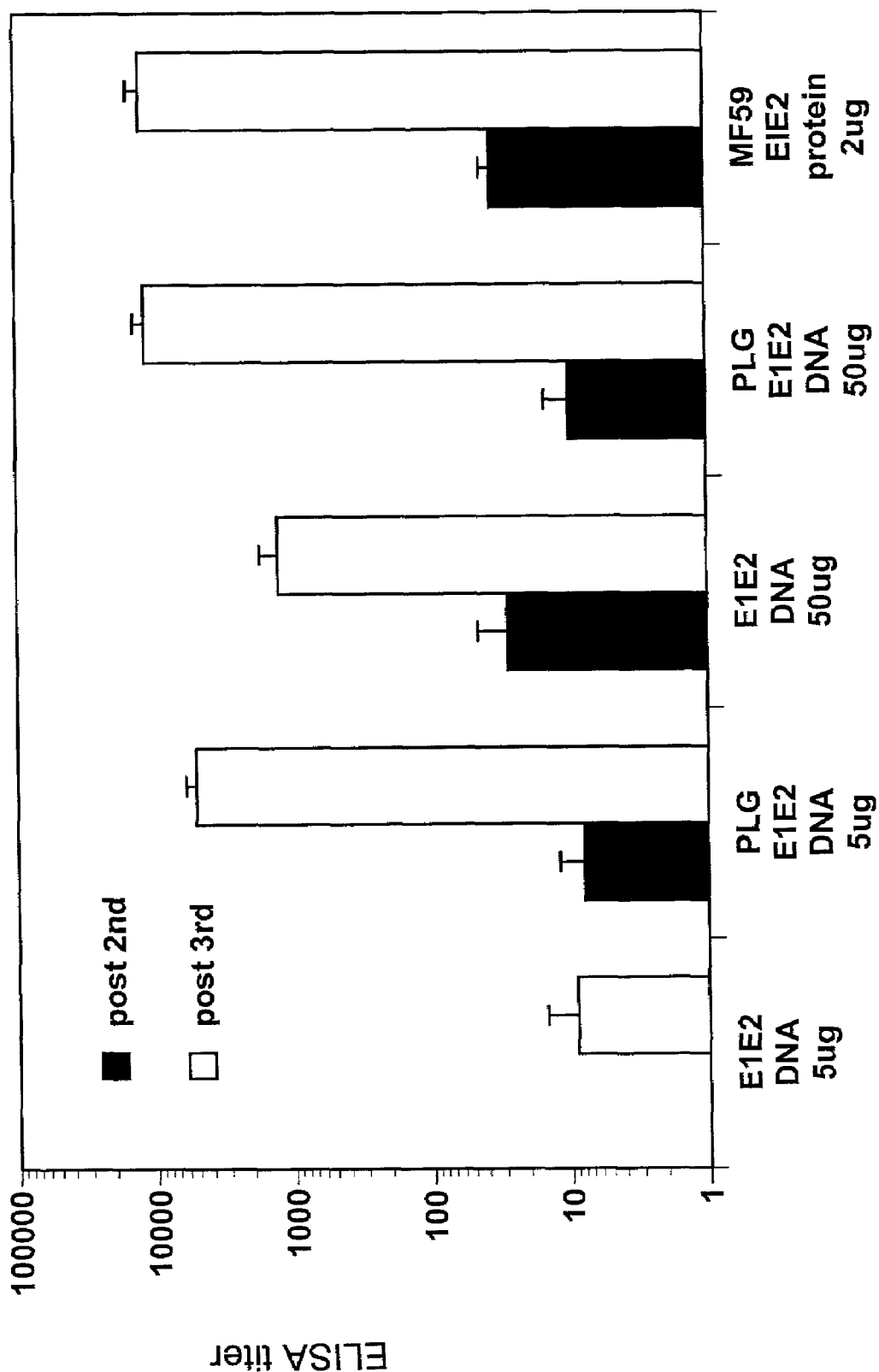
FIGS. 3 and 4 are graphs depicting ELISA titers of mice immunized with E1E2 DNA and/or protein in various adjuvants. The black bars depict titers post-2nd boost and the white bars depict titers post-3rd boost.
Figure 4:
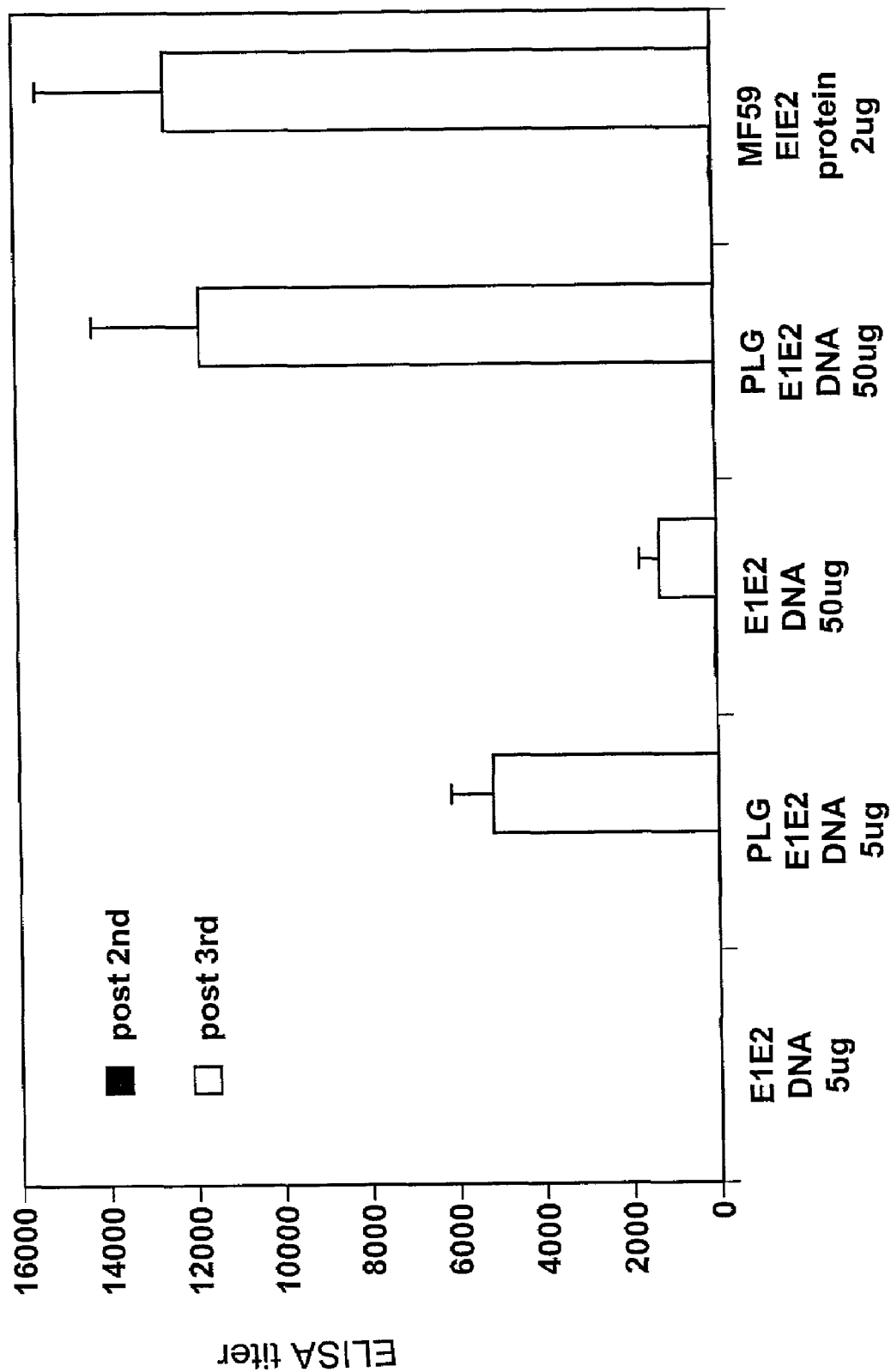

Antibody titers were measured by ELISA assays as described in herein. FIGS. 1 and 2 show the results of PLG immunization using the following DNA constructs: constructs encoding amino acids 384-746 (E2) and 192-746 (E1E2) of an HCV polyprotein. FIGS. 3 and 4 show the results of PLG immunizations using constructs encoding amino acids 384-749 (E2) and 192-749 (E1E2) of an HCV polyprotein. The results demonstrate that immunization of mice using PLG/E1E2 DNA results in high antibody titers.

We claim:

1. A method of eliciting a humoral immune response against a hepatitis C virus (HCV) E2 or E1E2 antigen comprising the step of (a) administering to a subject (i) a composition comprising an isolated polynucleotide encoding an HCV E1E2 antigen, wherein the E1E2 antigen consists of an HCV E1 polypeptide and an HCV E2 polypeptide and optionally an HCV p7 polypeptide, and further wherein the E1E2 antigen encoded by the polynucleotide consists of a sequence selected from the group consisting of a sequence of amino acids corresponding to amino acids 192-715 and optionally amino acids 747-809 numbered relative to the HCV-1 polyprotein, a sequence of amino acids corresponding to amino acids 192-661 and optionally amino acids 747-809 numbered relative to the HCV-1 polyprotein, and a sequence of amino acids corresponding to amino acids 192-674 and optionally amino acids 747-809 numbered relative to the HCV-1 polyprotein, or (ii) a composition comprising an isolated polynucleotide encoding a truncated E2 antigen, wherein said truncated E2 antigen does not include the p7 polypeptide, wherein the E2 antigen encoded by the polynucleotide consists of a sequence selected from the group consisting of a sequence of amino acids corresponding to amino acids 384-715 numbered relative to the HCV-1 polyprotein, a sequence of amino acids corresponding to amino acids 384-661 numbered relative to the HCV-1 polyprotein, and a sequence of amino acids corresponding to amino acids 384-674 numbered relative to the HCV-1 polyprotein, wherein the E2 or E1E2 antigen encoded by the polynucleotide is produced intracellularly and not secreted when expressed in cells of the subject.

2. The method of claim 1, wherein the humoral immune response generates at least one neutralization of binding (NOB) antibody.

3. The method of claims 1 or 2, wherein the composition comprises an isolated polynucleotide that encodes an E1E2 antigen, wherein the E1E2 antigen consists of an HCV E1 polypeptide and an HCV E2 polypeptide and optionally an HCV p7 polypeptide.

4. The method of claims 1 or 2, wherein the composition comprises an isolated polynucleotide that encodes a full-length E2 antigen.

5. The method of claims 1 or 2, wherein the HCV E1E2 antigen does not comprise a p7 polypeptide.

6. The method of claims 1 or 2, wherein the polynucleotide is in a plasmid.

7. The method of claims 1 or 2, wherein the subject is infected with an HCV.

8. The method of claims 1 or 2, wherein the subject is not infected with an HCV.

9. The method of claims 1 or 2, further comprising the step of administering cardiotoxin to the subject.

10. The method of claims 1 or 2, wherein the polynucleotide is administered using a microparticle.

11. The method of claim 10, wherein the microparticle is a poly(D,L-lactide-co-glycolide) (PLG) microparticle.

12. The method of claims 1 or 2, wherein the subject is a mammal.

13. The method of claim 12, wherein the mammal is selected from the group consisting of a mouse, a rabbit, a guinea pig, a macaque, a baboon, a chimpanzee, and a human.

14. The method of claims 1 or 2, wherein the polynucleotide is administered using a biolistic delivery device.

15. The method of claims 1 or 2, wherein the polynucleotide is administered by a method selected from the group consisting of intramuscular, subcutaneous, intraperitoneal, intranasal, oral, and intradermal administration.

16. The method of claim 2, wherein the neutralizing of binding antibody inhibits binding of an E2 polypeptide to its cognate receptor by an amount which is greater relative to binding of the E2 polypeptide to its cognate receptor in the absence of the neutralizing of binding antibody.

17. The method of claim 2, further comprising the step of detecting the neutralizing of binding antibody.

18. The method of claim 2, wherein the neutralizing of binding antibody inhibits binding of the E2 polypeptide by at least 50% at a dilution of at least 1:70.

19. The method of claim 2, wherein the neutralizing of binding antibody inhibits binding of the E2 polypeptide by at least 50% at a dilution of at least 1:140.

20. The method of claim 2, wherein the neutralizing of binding antibody inhibits binding of the E2 polypeptide by at least 50% at a dilution of at least 1:300.

21. The method of claim 2 wherein the neutralizing of binding antibody inhibits binding of the E2 polypeptide by at least 50% at a dilution of at least 1:600.

22. The method of claim 2, wherein the neutralizing of binding antibody inhibits binding of the E2 polypeptide by at least 50% at a dilution of at least 1:800.

23. The method of claim 2, wherein the neutralizing of binding antibody inhibits binding of the E2 polypeptide by at least 50% at a dilution of at least 1:3,000.

24. The method of claims 1 or 2, further comprising repeating step (a).

25. The method of claims 1 or 2, further comprising administering to the subject a polypeptide encoded by the polynucleotide.

26. The method of claim 6, wherein the subject is infected with an HCV.

27. The method of claim 6, wherein the subject is not infected with an HCV.

28. The method of claim 6, further comprising the step of administering cardiotoxin to the subject.

29. The method of claim 7, further comprising the step of administering cardiotoxin to the subject.

30. The method of claim 8, further comprising the step of administering cardiotoxin to the subject.

31. The method of claim 6, wherein the polynucleotide is administered using a microparticle.

32. The method of claim 7, wherein the polynucleotide is administered using a microparticle.

33. The method of claim 8, wherein the polynucleotide is administered using a microparticle.

34. The method of claim 9, wherein the polynucleotide is administered using a microparticle.

35. The method of claim 31, wherein the microparticle is a poly(D,L-lactide-co-glycolide) (PLG) microparticle.

36. The method of claim 32, wherein the microparticle is a poly(D,L-lactide-co-glycolide) (PLG) microparticle.

37. The method of claim 33, wherein the microparticle is a poly(D,L-lactide-co-glycolide) (PLG) microparticle.

38. The method of claim 34, wherein the microparticle is a poly(D,L-lactide-co-glycolide) (PLG) microparticle.

39. The method of claim 11, wherein the subject is a mammal.

40. The method of claim 35, wherein the subject is a mammal.

41. The method of claim 36, wherein the subject is a mammal.

42. The method of claim 37, wherein the subject is a mammal.

43. The method of claim 38, wherein the subject is a mammal.

* * * * *